(12) United States Patent
Lipiński et al.

(10) Patent No.: US 8,426,221 B2
(45) Date of Patent: Apr. 23, 2013

(54) METHOD OF BINDING BACTERIAL LIPOPOLYSACCHARIDES TO A SOLID PHASE

(75) Inventors: Tomasz Lipiński, Wroclaw (PL); Jacek Rybka, Wroclaw (PL); Andrzej Gamian, Wroclaw (PL)

(73) Assignee: Instytut Immunologii I Terapii, Wroclaw (PL)

( * ) Notice: Subject to any disclaimer, the term of this patent is extended or adjusted under 35 U.S.C. 154(b) by 0 days.

(21) Appl. No.: 13/059,539

(22) PCT Filed: Sep. 27, 2009

(86) PCT No.: PCT/PL2009/050026
§ 371 (c)(1),
(2), (4) Date: May 3, 2011

(87) PCT Pub. No.: WO2010/036133
PCT Pub. Date: Apr. 1, 2010

(65) Prior Publication Data
US 2011/0230648 A1    Sep. 22, 2011

(30) Foreign Application Priority Data
Sep. 29, 2008 (PL) .......................... 386174

(51) Int. Cl.
*G01N 33/543* (2006.01)
(52) U.S. Cl.
USPC ........................................................ 436/518
(58) Field of Classification Search .................. None
See application file for complete search history.

(56) References Cited

FOREIGN PATENT DOCUMENTS
FR    2660197    10/1991
WO    0036419    6/2000

OTHER PUBLICATIONS

Fischer et al (Eur. J. Biochem, 194:655-661, 1990).*
Gamian Andrzej et al., "The occurrence of glycine in bacterial lipopolysaccharides" Fems Immunology and Medical Microbiology, vol. 13, No. 4, 1996, pp. 261-268.
Girard R. et al., "Preparation of monospecific anto-Salmonella lipopolysaccharide antibodies by affinity chromatography" Annales de L'Institut Pasteur. Immunologie, Elsevier, Paris, FR, vol. 132, No. 2, Mar. 1, 1981 pp. 211-217.
Romanowska E. et al., Lipopolysaccharide immunoadsorbents and their application to affinity chromatography of o-antibodies and specific phages: Febs Letters, Elsevier, Amsterdam, NL, vol. 66, No. 1, Jul. 1, 1976 , pp. 82-85.
International Search Report issued by the International Searching Authority (ISA/O.E.P.M.) on Nov. 2, 2010 in connection with International Application No. PCT/PL2009/050026.
International Preliminary Report on Patentability, issued on Mar. 29, 2011 in connection with International Application No. PCT/PL2009/050026.
Nov. 12, 2011 Amendment before Examination filed in connection with European Patent Application No. 09752002.7-2406, which is the European counterpart of the subject application.
Jul. 2, 2012 Communication from the Examining Division, issued in connection with European Patent Application No. 09752002.7-2406, which is the European counterpart of the subject application.

* cited by examiner

*Primary Examiner* — Patricia A Duffy
(74) *Attorney, Agent, or Firm* — Gary J. Gershik; Cooper & Dunham LLP

(57) ABSTRACT

The subject the present invention is a method of producing affinity beds with bacterial lipopolysaccharide molecules bound to them in a non-covalent and stable fashion. The bed produced according to the present invention may be used in affinity chromatography for the purification of antibodies against lipopolysaccharides. It is particularly useful in the purification of antibodies against the labile epitopes of lipopolysaccharides, which degrade in heretofore used methods of covalent bonding of the lipopolysaccharide molecules to the solid phase.

14 Claims, No Drawings

METHOD OF BINDING BACTERIAL LIPOPOLYSACCHARIDES TO A SOLID PHASE

The present invention relates to a permanent and non-covalent method of binding bacterial lipopolysaccharides to a solid phase. This method is useful in purification techniques, particularly chromatography techniques, particularly in the purification of antibodies.

A lipopolysaccharide (LPS, endotoxin) is a fundamental component of the external membrane of Gram-negative bacteria. An LPS molecule consists of a lipid portion (lipid A) anchoring it in the external membrane, and saccharide portions (LPS core as well as O-specific antigen), exposed directly to the external environment. This molecule is essential for the growth and viability of a bacterial the goal of, since it warrants the integrity of the goal of wall and protects it against deleterious external factors, such as too low or too high pH, detergents, antibiotics, bile salts or immune system components in the higher taxa. It is also a decisive factor of the virulence of Gram-negative bacteria and the mutual relationship of saprophytic bacteria and host organisms [1.2].

Lipid A has a unique structure [3], and is thus the most conserved portion of the LPS. The molecular skeleton is formed by a disaccharide composed of two β1→6-linked phosphorylated glucosamine (D-GlcN) molecules. The disaccharide is directly acylated (O- and N-acylated) with four molecules of 3-hydroxyl fatty acids (3-OH 14:0). The additional acylation of these —OH groups yields acyloxyacyl substituents. Lipid A isolates rarely constitute a single fraction. Modifications of the basal structure most often consist of changes in the number, properties and localisation of additional fatty acids (linked to the 3-hydroxy group), as polar substituents. For example, in salmonella the modifications are often not stoichiometric, which results in a the preparations being greatly heterogenic. For example, in Salmonella, a portion of the molecules contains an additional chain (16:0) acylating the OH group of the 3-hydroxyl bound at position 2 to the GlcN, whereas in other molecules a portion of the additional molecules of myristic acid is substituted by 2-hydroxytetradecanoic [4].

The O-specific antigen is a polysaccharide composed of repeating oligosaccharide units of one to eight sugar residues. The O-specific antigen in bacteria lacking a wall is the chief surface antigen warranting their serological specificity. It is characterised by its extensive variability. The large variety of possible structures endowed by common sugars such as glucose, mannose and glactose is greatly enhanced through the use of sugars of varying chain length, from 4 to 10, pyranose and furanose forms, various stereoisomers and chemical modifications such as deoxy, amino or carboxyl, estrification, etherification, acetylation and amidation. Furthermore, branched sugars also occur, as well as non-sugar components such as phosphate residues and amino-acids. The most commonly seen modifications of O-specific antigens include O-acetylation, phosphorylation of O-methylation. Other ether groups include the carboxyethyl group. Amine functionalities of aminosaccharides are most often modified with an acetyl or other, less typical substituents [5].

The LPS core is the oligosaccharide connecting lipid A to the O-specific antigen. A structural comparison of core structures known to date shows that, second to lipid A ,thus is the most conserved part of the LPS. It is characterised by the presence of two atypical sugars: 3-deoxy-D-manno-2-octulopyranosonoic (Kdo) acid and heptopyranose (Hepp). The heptose may occur both in an L-glyceryl-D-manno (L,D) and D-glyceryl-D-manno (D,D) forms. Most LPS variants contain only one form of the heptose. For example the cores of *E. coli*, *S. minnesota* contain solely the L,D form. Others may contain both (*Proteus mirabilis*, *Yersinia enterocolytica*) or only D,D heptose (some phototrophic bacteria). Species lacking the heptose are also known, such as *Bacteroides fragilis* [184]. Amino-acids are sometimes found in the core preparations of core oligosaccharides. They may be amide-linked to uronic acids, threonine u *Rhodobacter sphaeroides*. Sometimes they constitute N-acyl groups with hexoses, i.e. alanine in *Pseudomonas aeruginosa*, however, most of the time this is ester-linked glycine in core oligosaccharides.

The large similarity of core structures in many bacteria has made many researchers to study the possibilities of antibodies and sera capable of cross-reacting between the LPSs of many species of bacteria. The research sometimes made use of mutants lacking antigen O (rough). Polyclonal anti-core sera have been obtained by immunising animals with cells of *E. coli* O111, the Rc mutant, and *S. enterica*, chemotype Re [6]. The lipopolysaccharide is the main factor which induces inflammation, and is thus an important factor in immunological research. It is also an important molecule in diagnostics and is a substrate for synthetic conjugated vaccines.

Known from prior art are methods of purifying antibodies directed against lipopolysaccharide epitopes, which make use of covalent bonding of lipopolysaccharide molecules to a solid phase.

One of the concepts of preventing and treating sepsis caused by Gram-negative bacteria stipulates the production of widely cross-reactive antibodies against the lipopolysaccharides of many bacteria. Conditional to obtaining these is to find common, shared epitopes within the LPS, such as those constituting the non-sugar components of lipopolysaccharides. These components occur particularly often in the core portion of LPS. These comprise phosphates, pyrophosphates, ethanolamine, pyrophosphoethanolamine, acyl groups and others. They are often in non-stoichiometric quantities, and are often chemically labile. Such groups are easily lost during LPS extraction and subsequent chemical modifications, which complicates the determination of their biological significance and the production of antibodies against epitopes that contain them. The Applicant's research has resulted in the discovery of glycine as a non-sugar substituent of lipopolysaccharides. Glycine is connected with the core oligosaccharide and commonly occurs in LPS. Significant data has been obtained which suggests that it participates in forming the epitope present in the lipopolysaccharides of many Gram-negative bacteria. Glycine is present in the core portion and, when it is a part of the common epitope, may be a substrate for a wide-spectrum vaccine [7].

In an aqueous environment, lipopolysaccharide forms an opalescent suspension, since it is an insoluble substance due to the lipid character of the molecules, further cross-linked by the activity of phosphate and amine functionalities with metal ions. An increase of the solubility and the production of LPS in the form of a homogenous and transparent solution may be obtained via several methods, through the removal of bivalent metals. In the present invention, soluble LPS was obtained the described procedure. Other methods are also known, such as electrodialysis used to produce various LPS salts [9], the use of a chelator such as EDTA or Chelex gel to improve electrophoretic separations of LPS and the removal of paramagnetic ions during the recording of NMR spectra NMR [10].

In light of the above prior art, the objective technical problem in need of a solution is to obtain a method of producing antibodies and sera capable of cross-reacting with the LPSs of many bacterial species.

The extant methods of immobilising LPS via chemical methods, such as binding to bromocyanate-activated Sepharose 4B gel [8], cause the labile structures responsible for biological activity to degrade.

The goal of the present invention is to obtain labile structures responsible for the biological activity of endotoxins, which enable the production of antibodies specific against native endotoxins, purified on columns containing native endotoxins.

Antibodies purified on columns containing native endotoxins are useful not only in the diagnostics and isolation of native LPS structures, but also as unique reagents for immunochemical research. Affinity columns produced via the method according to the present invention make it possible to produce heretofore unavailable, highly specific antibodies and unique ones with a broad activity range. Finally, affinity columns according to the present invention make it possible to isolate specific phages and phage preparations specific for immobilised receptors. To date such a tool has been unavailable due to the degradation of labile phage receptors during the immobilisation.

The goal of the present invention is a method of producing a bed for affinity chromatography bacterial LPS molecules bound to it in a non-covalent and permanent fashion, characterised in that the lipopolysaccharide is solubilised in water, the soluble LPS preparation is transformed into its acid form which is then dissolved in an organic solvent and the LPS in this solution is immobilised on the bed, which contains a solid phase modified with hydrophobic groups, where the LPS molecules form hydrophobic bonds with aliphatic chains.

The next goal of the present invention is the use of such a bed for the production of anti-LPS antibodies.

Preferentially, the subject of the present invention is a use, characterised in that the bed is used to purify antibodies against labile LPS epitopes.

This description reveals a method of producing an affinity matrix composed of a solid phase conjugated in a non-covalent but permanent fashion with LPS, which may be used in the isolation of antibodies, particularly those directed against epitopes containing labile components such as glycine.

Preferentially, such a bed can have other uses which make use of LPS non-covalently bonded to a solid phase without the loss of labile substituents. Matrices of non-covalently immobilised lipopolysaccharides are useful in many applications in biotechnology, medicine, pharmacology and diagnostics. The immobilisation of native endotoxins is essential in cases when it is necessary to conserve the labile bonds of sialic acids, acetyl residues, phosphate esters and others. Such labile groups occur in the endotoxins of *Neisseria, Haemophilus, Shigella* and many others, used as substrates in conjugated vaccines. Affinity columns produced according to the present invention are used in the rapid isolation of antibodies, making it possible to perform the entire procedure of preparing the column and purifying the antibodies in several hours. Such columns are used in the single-stage preparation of mono-specific as well as monoclonal, anti-endotoxin as well as anti-glycolipid antibodies. The procedure of preparing columns according to the present invention does not require unsafe reagents such as bromocyanate. The method according to the present invention is simple, inexpensive, efficient, economic and safe, and yields a stable and non-toxic product ready for immediate use and technological application, as well as broad commercialisation.

The crux of the present invention is a method of forming a solid phase modified with LPS in a non-covalent fashion, under conditions which do not damage labile substituents. The labile substituents of endotoxins often interact with antibodies and phages, thus labile epitopes are components of vaccines and diagnostics. Labile epitopes are important determinants are used in the construction of conjugated vaccines. Lipopolysaccharides are insoluble, and form a suspension in an aqueous environment. The novelty of the present invention consists of the production of soluble lipopolysaccharides and some organic solvents, warranting the immobilisation of the LPS on a gel. The disclosed method consists of transforming the LPS into a water-soluble form and also in organic solvents as well as the immobilisation of such an LPS on a solid phase. The method of transforming the lipopolysaccharide into the active form consists of reacting the LPS with factors initially facilitating the dissociation of LPS complexes in water, and then of the removal of bivalent metal ions from the LPS preparation using a chelator, as well as transforming the lipopolysaccharide into a form soluble in the organic solvent. Unexpectedly, it was determined that only the soluble form of LPS strongly and stably immobilises on a hydrophobic gel. Native LPS is not immobilised effectively and binds to the gel poorly, and thus is easily eluted and likely forms superstructural aggregates in an aqueous solution. It was determined that the form soluble in the organic solvent warrants immobilisation of such an LPS on a solid phase modified with alkyl chains. To date, LPS was immobilised using chemical methods, which degrade the labile structures responsible for biological activity, such as the method of binding to a bromocyanate-activated Sepharose 4B [8]. The novelty of the present invention further consists of the use of BSA to block free sites on the gel. This protein is a natural fatty acid carrier, used in ELISA assays. In the present invention it was used successfully to permanently and stably block free sites on the affinity matrix. Due to this property of BSA, the aliphatic chains of LPS bind stably to the gel, additionally stabilising the LPS-C18 chromatography system. A significant element of the present invention is also the observation that LPS soluble in DMSO, water, or another organic solvent is immobilised on the gel in the very same environment of DMSO or other organic solvent.

Preferentially, the factor enhancing the dissociation of lipopolysaccharide complexes in water is a detergent such as a dodecyl sulphate (SDS).

Preferentially, the factor removing bivalent ions cross-linking the lipopolysaccharide, is ethylenediaminotetraacetic acid (versenic acid, EDTA), a solid phase matrix such as Chelex or electrodialysis.

Preferentially, the soluble form of the native lipopolysaccharide consists of its salts (i.e. sodium or tert-butylamine salt), an acidic form of the lipopolysaccharide: LPS Ft or a lipopolysaccharide modified chemically (i.e. N-acetylated).

Preferentially, the solvents used to dissolve an appropriate form of the lipopolysaccharide is water, methanol, dimethylsulfoxide, dichloromethane or acetonitrile.

Preferentially, the solid phase for immobilising the soluble LPS is a silica gel with covalently bound alkyl groups, preferentially octadecyl groups.

The method of transforming the lipopolysaccharide into the soluble form as a substrate for affinity chromatography encompasses the removal of bivalent metal ions from the lipopolysaccharide preparation, where the lipopolysaccharide preparation is first treated with a detergent, preferentially and ionic detergent such as dodecylsulphate, and then treated with a chelator which removes bivalent metal ions, preferentially a substance such as a polycarboxylic acid (i.e. EDTA) or a Chelex-type matrix based on a synthetic resin, or another process leading to the removal of bivalent metal ions from the preparation (i.e. electrodialysis).

Preferentially, during the removal of the detergent and chelator, the lipopolysaccharide is precipitated out of the solution using an organic solvent, preferentially ethanol, and then the precipitated soluble LPS preparation is dried without liophilising.

The lipopolysaccharide is transformed into its acidic form, where the solution of the soluble lipopolysaccharide is treated with a factor which replaces monovalent metal ions ($Na^+$, $K^+$) in the neutral LPS salt with acidic protons (Ft), preferentially on an ion exchange matrix based on a synthetic resin.

Preferentially, a homogenous solution of the lipopolysaccharide is formed in a polar solvent, particularly an organic solvent, where the acidic form of the LPS is dissolved in the organic solvent, preferentially water or dimethylsulfoxide (DMSO).

Preparation of the solid phase with the immobilised lipopolysaccharide is characterised in that the modified lipopolysaccharide is dissolved in the solvent, preferentially, water or DMSO, is bound to the solid phase possessing a surface modified with hydrophobic groups, preferentially alkyl chains such as octadecyl chains ($C_{18}$) through hydrophobic interactions between the fatty acid chains of the lipopolysaccharide a and the hydrophobic groups of the solid phase.

During the production of the solid phase with the immobilised lipopolysaccharide, the modified LPS, preferentially dissolved in a solvent, preferentially water or DMSO, is bound to the solid phase through the addition of the matrix to the LPS solution.

During the production of the solid phase with the immobilised lipopolysaccharide, the solid phase with the immobilised LPS is preferentially blocked with BSA.

Examples of transforming endotoxin preparations into a soluble form in organic solvents, of binding such a form to a solid phase, and the use of the resulting of such an affinity phase in the purification of anti-LPS antibodies.

EXAMPLE 1

In this example, a chromatography affinity bed was made for the purification of antibodies against the rough lipopolysaccharide of the *E. coli* strain K12 C600. A sample of the lyophilised LPS of *E. coli* K12 C600 (20 mg) was dissolved in 2 ml 2% SDS, and then 0.2 ml 0.5 M EDTA were added. After 10 min. it was centrifuged for 20 min. at 5000 RPM. The precipitate was disposed of, and the LPS solution was supplemented with 4 volumes of ethanol, chilled to −20° C. and recentrifuged (5000 RPM, 20 min.). The formed precipitate was suspended in a 3:1 ethanol:water mixture, recentrifuged (5000 RPM, 20 min), the procedure was repeated twice. After the final centrifugation, the precipitate was dried in a dessicator. The dried precipitate was dissolved in water (2 ml) and passed through a column of Dowex 50W-X8 (2 ml) equilibrated with $H^+$ ions, whereafter the column was rinsed in MiliQ water until a neutral eluate was obtained. The collected eluate was lyophilised and then dissolved in DMSO (5 ml). The prepared solution was supplemented with SilicaGel C18, incubated for 18 hours with continuous mixing. Unbound lipopolysaccharide was eluted with DMSO and then 50% methanol.

EXAMPLE 2

This example ten relates to the production of an affinity bed for chromatography for the purification of antibodies against the lipopolysaccharide of *E. coli* K12 C600, where the factor removing the factor used to remove bivalent metal ions from the LPS preparation LPS was a Chelex gel equilibrated with $Na^+$ ions. A sample of the lyophilised LPS of *E. coli* K12 C600 (20 mg) was dissolved in 2 ml 2% SDS, centrifuged (20 min, 5000 RPM), and passed through a column (1 ml) of Chelex, which was then rinsed with 5 ml of water. Ethanol precipitation as well as the remainder of the procedure were as in Example 1.

EXAMPLE 3

This example relates to the production of a affinity chromatography bed for the purification of antibodies against the lipopolysaccharide of *E. coli* K12 C600, where the solid phase for binding the lipopolysaccharide was the gel octyl-Sepharose CL-4B, whereas the remaining procedure was identical to that in Example 1.

EXAMPLE 4

This example relates to the production of an affinity chromatography bed for the purification of antibodies against the lipopolysaccharide of *E. coli* K12 C600, where the soluble form of the lipopolysaccharide was the tertbutyloamine salt (TBA) of the LPS, whereas the remaining procedure was identical to that in Example 1.

EXAMPLE 5

This example relates to the production of an affinity chromatography bed for the purification of antibodies against the lipopolysaccharide of *E. coli* K12 C600, where the soluble form of the lipopolysaccharide was dissolved in methanol and then the procedure of binding the LPS to a SilicaGel C18 bed was performed, and the remaining procedure was identical to that in Example 1.

EXAMPLE 6

This example relates to the production of affinity chromatography beds for the purification of antibodies, in which the production of an a soluble form of the lipopolysaccharides was performed using two lipopolysaccharides from *H. alvei* PCM 1186 and *H. alvei* PCM 1189, the remaining procedure was identical to that in Example 1.

The remaining beds suspended in 50% methanol were packed into two columns of 0.5×5.0 cm (1 cm³). The columns were rinsed with water and PBS, whereafter each one was rinsed with 10 ml of 1% BSA in PBS and then PBS until no absorbance at X=280 nm could be detected.

Prior to the affinity chromatography immunoglobulins were isolated from anti-LPS sera by ammonium acid precipitation. The precipitation was performed as follows. 5 ml of rabbit anti-Hafnia alvei 1186 or anti-Hafnia alvei PCM 1189 serum was diluted in 10 ml PBS. With constant mixing, 4.8 g of ammonium sulphate was added dropwise. After the last of it was added, the serum was incubated for 60 minutes in an ice water bath. The precipitate was centrifuged at 10000 g and 5° C. for 30 minutes. The precipitate was dissolved in 5 ml PBS and dialysed at 4° C. into PBS as well as into PBS with 0.02% sodium azide.

The precipitated antibodies were then purified by affinity chromatography. Dialised preparations of the appropriate precipitated antibodies were loaded onto columns containing the solid phase with bound native LPS. Unbound proteins were eluted with PBS (fraction 1), antibodies with an affinity for the antigen were eluted using 3M KSCN in PBS (fraction 2). The No. 2 fractions of both columns were dialysed against PBS and condensed using ultrafiltration.

The specificity of the antibodies was evaluated using an ELISA assay where the test plates were coated with the lipopolysaccharides of *H. alvei* PCM 1186 and *H. alvei* PCM 1189 and the affinity of both antibodies to the immobilised LPSs was measured (fractions No. 2 following chromatography in both columns). Antibodies showed a high affinity for lipopolysaccharides in homogenous systems (respectively antibody a-1186 for the LPS of *H. alvei* PCM 1186 as well as antibody a-1189 for the LPS of *H. alvei* PCM 1189), whereas no cross-reactivity was observed of the antibodies with these lipopolysaccharides.

EXAMPLE 7

This example relates to the purification of specific antibodies against epitopes of lipopolysaccharides containing labile substituents of glycine. Two preparations of the lipopolysaccharide of *E. coli* K12 C600 were used: a native one and one with the glycine removed (the lipopolysaccharide dissolved in water at a rate of 0.5 mg/ml was subjected to ammonia in water, pH 12, for 12 hours at room temperature, and then purified on a Sephadex G-25 Superfine gel in water and liophilised). The procedure for the production of an affinity chromatography bed for the purification of antibodies is identical to that of Example 1. The resulting gels suspended in 50% methanol were packed into two columns of 0.5×5.0 cm (1 cm3). The columns were rinsed with water and PBS, whereafter each one was rinsed with 10 ml of 1% BSA in PBS and then PBS until no absorbance at X=280 nm could be detected.

The precipitation was performed as follows. 5 ml of rabbit serum against *E. coli* K12 C600 were diluted in 10 ml PBS. With constant mixing, 9.6 g of ammonium sulphate was added dropwise. After the last of it was added, the serum was incubated for 60 minutes in an ice water bath with constant mixing. The precipitate was centrifuged at 3000 g and 25° C. for 30 minutes. The precipitate was dissolved in 5 ml PBS and dialysed at 4° C. into PBS.

The dialysed preparation of the precipitated antibody was loaded onto a column containing the bound native LPS. Unbound proteins were eluted with PBS (fraction 1), antibodies with a weak affinity for the antigen were eluted using 3 M KSCN in PBS (fraction 2). High-affinity antibodies were eluted with 3 M KSCN w PBS (fraction 3). Fraction 3 was dialysed against PBS, concentrated using ultrafiltration and loaded onto a column with a solid phase bound with deglycinated LPS. The chromatography was performed as described above. The antibodies of fraction 1, not binding deglycinated LPS possessed an affinity for epitopes containing glycine.

LITERATURE

1. Schletter J., Heine H., Ulmer A. J., Rietschel E. T. (1995), Molecular mechanisms of endotoxin activity. *Arch Microbiol*, 164, 383-389.
2. Rietschel E. T., Kirikae T., Schade F. U., Ulmer A. J., Holst O., Brade H., Schmidt G., Mamat U., Grimmecke H. D., Kusumoto S. (1993), The chemical structure of bacterial endotoxin in relation to bioactivity. *Immunobiology*, 187, 169-190.
3. Rietschel E. T., Wollenweber H. W., Russa R., Brade H., Zahringer U. (1984), Concepts of the chemical structure of lipid A. *Rev Infect Dis*, 6, 432-438.
4. Zahringer U., Lindner B., Rietschel E. T. (1994), Molecular structure of lipid A, the endotoxic center of bacterial lipopolysaccharides. *Adv Carbohydr Chem Biochem*, 50, 211-276.
5. Wilkinson S. G. (1996), Bacterial lipopolysaccharides themes and variations. *Prog Lipid Res*, 35, 283-343.
6 Rietschel E. T., Brade H., Holst O., Brade L., Muller L. S., Mamat U., Zahringer U., Beckmann F., Seydel U., Brandenburg K., Ulmer A. J., Mattern T., Heine H., Schletter J., Loppnow H., Schonbeck U., Flad H. D., Hauschildt S., Schade U. F., Di Padova F., Kusumoto S., Schumann R. R. (1996), Bacterial endotoxin: Chemical constitution, biological recognition, host response, and immunological detoxification. *Curr Top Microbiol Immunol*, 216, 39-81.
7 Gamian A., Mieszala M., Boratynski J., A method wytwarzania szczepionki koniugatowej o szerokiej swoistoki przeciwbakteryjnej, Zgl. Pat. Nr 328280 z dn. 31. 08. 1998 r., Patent PL nr 192872 z dnia 27. 03. 2006.
8 Romanowska E, Lugowski C, Mulczyk M. (1976), Lipopolysaccharide immunoadsorbents and their application to affinity chromatography of O-antibodies and specific phages. *FEBS Lett*, 66, 82-85.
9 Galanos C., Luderitz O. (1975), Electrodialysis of lipopolysaccharides and their conversion to uniform salt forms, *Eur J Biochem*, 54, 603-610.
10 Mansson M., Bauer S. H. J., Hood D. W., Richards J. C., Moxon E. R., Schweda E. K. H. (2001), A new structural type for *Haemophilus influenzae* lipopolysaccharide. Structural analysis of the lipopolysaccharide from non-typeable *Haemophilus influenzae* strain 486, *Eur J Biochem*, 268, 2148-2159.

The invention claimed is:

1. A process for producing a bed for affinity chromatography, which bed comprises non-covalently and stably bound bacterial lipopolysaccharide (LPS), the method comprising:
   i) transforming the LPS into a water-soluble form;
   ii) transforming the water-soluble LPS into an acidic form in an organic solvent;
   iii) immobilizing the LPS in the organic solvent on a gel whose solid phase has hydrophobic groups comprising aliphatic chains, wherein the LPS hydrophobically interacts with aliphatic chains of the solid phase in the gel, such that the LPS is non-covalently and stably bound to the solid phase.

2. The process of claim 1, further comprising a step of blocking sites of hydrophobic groups of the solid phase of the gel that are not bound to LPS by rinsing the gel with a bovine serum albumin (BSA) solution.

3. The process of claim 1, wherein the LPS that is non-covalently and stably bound to the solid phase of the gel comprises a chemically labile component that is present in the native form of the LPS.

4. The process of claim 1, wherein the LPS is non-covalently and stably bound to the solid phase of the gel such that the LPS does not elute from the gel in the presence of 3M KSCN.

5. The process of claim 1, wherein immobilization of the LPS in step iii) occurs in the organic solvent of step ii).

6. The process of claim 5, wherein the organic solvent is dimethylsulfoxide (DMSO).

7. The process of claim 5, wherein the organic solvent is methanol.

8. The process of claim 1, wherein the aliphatic chains are octadecyl chains.

9. The process of claim 3, wherein the chemically labile component is a glycine which is present in the core portion of the LPS.

10. The process of claim 1, wherein step i) further comprises dissolving the LPS in dodecyl sulphate (SDS).

11. The process of claim 10, wherein in step i) transforming the LPS into a water-soluble form comprises a chelator.

12. The process of claim 11, wherein the chelator is ethylenediaminetetraacetic acid (EDTA) or Chelex.

13. the process of claim 11, wherein step ii) comprises:
   a) precipitating the LPS out of the solution containing the detergent using ethanol;
   b) drying the precipitated LPS to remove the ethanol and dissolving the dried LPS in water;
   c) passing the LPS through a Dowex column equilibrated with H' ions;
   d) lyophilizing the LPS eluted from the Dowex column to remove the water; and
   e) dissolving the LPS in DMSO.

14. The process of claim 1, wherein the gel is blocked with bovine serum albumin.

* * * * *